(12) United States Patent
Ramakrishna et al.

(10) Patent No.: US 9,155,979 B2
(45) Date of Patent: Oct. 13, 2015

(54) METHOD FOR PERFORMING MAINTENANCE ON A CHROMATOGRAPHY COLUMN

(71) Applicant: GE HEALTHCARE BIO-SCIENCES AB, Uppsala (SE)

(72) Inventors: Manoj Kumar Ramakrishna, Bangalore (IN); Daniel Salomonsson, Uppsala (SE); Per Uselius, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 36 days.

(21) Appl. No.: 14/159,046

(22) Filed: Jan. 20, 2014

(65) Prior Publication Data

US 2014/0131266 A1    May 15, 2014

Related U.S. Application Data

(62) Division of application No. 13/703,388, filed as application No. PCT/SE2011/050746 on Jun. 16, 2011, now Pat. No. 8,668,829.

(30) Foreign Application Priority Data

Jun. 23, 2010    (IN) .......................... 1457/DEL/2010

(51) Int. Cl.
  *B01D 15/10*    (2006.01)
  *B01D 15/22*    (2006.01)
  *G01N 30/56*    (2006.01)

(52) U.S. Cl.
  CPC ............... *B01D 15/10* (2013.01); *B01D 15/22* (2013.01); *G01N 30/56* (2013.01); *Y10T 29/49721* (2015.01)

(58) Field of Classification Search
  CPC ........ B01D 15/10; B01D 15/22; G01N 30/56; Y10T 29/49721
  USPC ................... 210/635, 656, 659, 198.2; 95/82; 96/101
  See application file for complete search history.

(56) References Cited

U.S. PATENT DOCUMENTS

| 6,736,974 B1 | 5/2004 | Mann |
| 2007/0138098 A1 | 6/2007 | Spencer |

FOREIGN PATENT DOCUMENTS

| WO | WO 2006/048058 | 5/2006 |
| WO | WO 2009/093952 | 7/2009 |

OTHER PUBLICATIONS

Search Report Dated Apr. 23, 2014 Issued on Corresponding CN Application No. 201180030700.X.

*Primary Examiner* — Ernest G Therkorn
(74) *Attorney, Agent, or Firm* — Parks Wood LLC (57) ABSTRACT

A method for performing maintenance on a chromatography column (1; 41) comprising the steps of:
a) when maintenance is required, detaching a detachable joint (7; 63) between a bottom plate (5; 53) of the chromatography column and a stand (3; 43) on which the chromatography column is provided;
b) attaching an adaptor (15; 59) provided in the chromatography system to any part of the chromatography column (1; 41) making it possible to lift the bottom plate (5; 53) from the stand (3; 43) with the adaptor (15; 59); and
c) raising the adaptor (15; 59) and thereby also the bottom plate (5; 53) such that maintenance can be performed under the bottom plate (5; 53).

2 Claims, 11 Drawing Sheets

METHOD FOR PERFORMING MAINTENANCE ON A CHROMATOGRAPHY COLUMN

TECHNICAL FIELD OF THE INVENTION

The present invention relates to a method for performing maintenance on a chromatography column and to a chromatography system.

BACKGROUND OF THE INVENTION

Some parts of a chromatography column need to be cleaned or replaced regularly. For example access is needed beneath a bottom plate of the chromatography column to change a valve provided there. Usually there is not much space between the bottom plate and the floor because it is preferable to keep the overall height of the chromatography column as small as possible. Because of the limited space below the bottom plate it is tricky to get access to the bolts and valves that need to be accessed.

SUMMARY

An object of the present invention is to solve the problems described above related to prior art.

This is achieved in a chromatography system according to claims.

Hereby an operator will get good access to the underside of the bottom plate and at the same time the overall height of the chromatography column can be kept at a minimum.

Suitable embodiments are described in the dependent claims.

DETAILED DESCRIPTION OF THE EMBODIMENTS

Figure 1A:
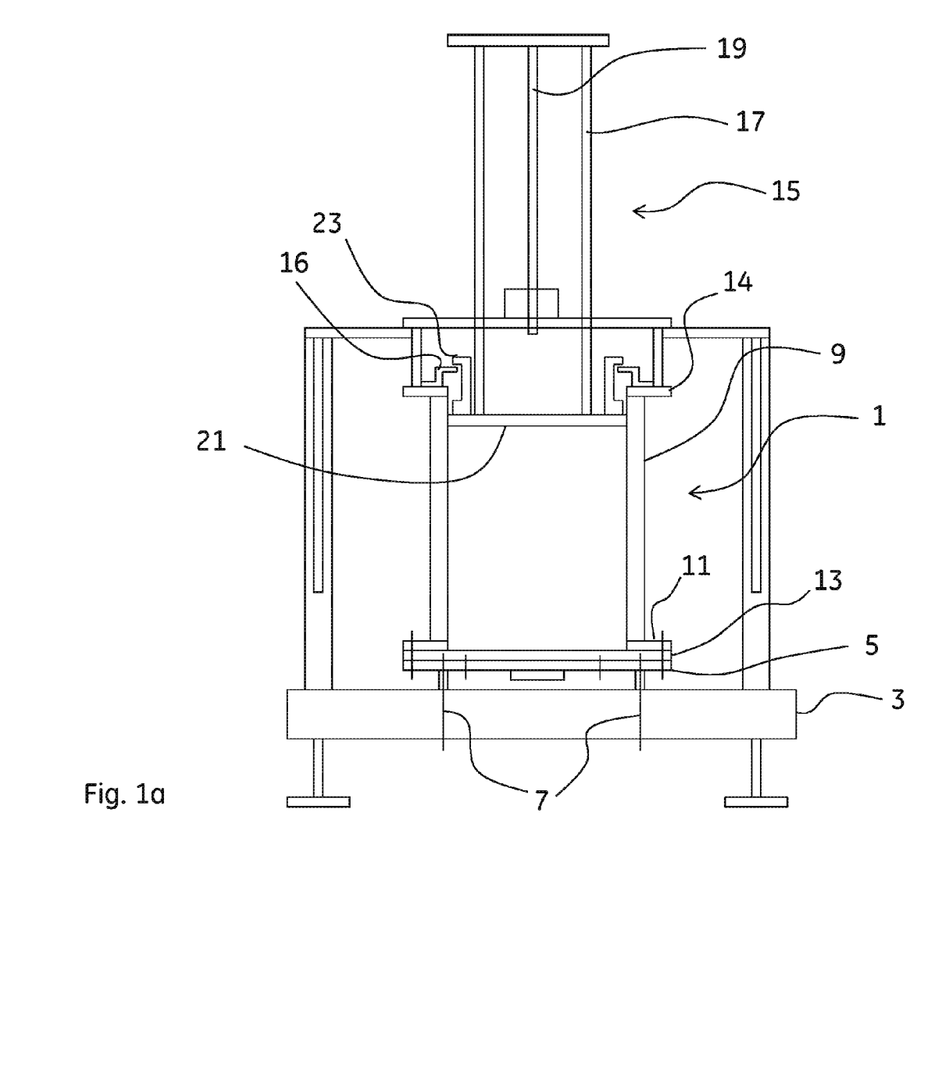
FIGS. 1a-1c show schematically a chromatography system according to one embodiment of the invention in three different positions.

FIG. 1a shows schematically a chromatography system according to one embodiment of the invention. All the parts are not mentioned here but they are conventional parts of a chromatography system. A chromatography column 1 is provided on a stand 3. According to the invention a bottom plate 5 of the chromatography column is detachably secured with a detachable joint 7 to the stand 3. In this embodiment the detachable joint 7 is shown as two bolts 7 securing the bottom plate 5 to the stand 3. One example of a detachable joint is shown in more detail in FIG. 1d. The chromatography column 1 comprises further a column tube 9, connected at its bottom end to a bottom flange 11, a distributor 13 and the bottom plate 5. The column tube 9 is connected at its upper end to an upper flange 14. Furthermore an adaptor 15 is provided in the chromatography system. According to the invention the adaptor 15 can be secured to the chromatography column 1 by a locking means 16. The adaptor 15 comprises an adaptor rod 17, a worm gear 19, an adaptor backing plate 21 and an adaptor stop 23. The adaptor stop 23 is provided in order to secure that the adaptor backing plate 21 will not be lifted above the column tube 9. In this embodiment of the invention a locking means 16 is provided to the upper flange 14 and is adapted to engage with the adaptor stop 23 when the adaptor 15 is raised such that the whole column can be raised from the stand when the detachable joint 7 has been released. In an alternative embodiment where no adaptor stop 23 is provided the locking means 16 can instead be arranged to engage directly with the adaptor backing plate 21 when the adaptor 15 is raised when maintenance beneath the column is needed. The locking means 16 is detachable and will be removed when the adaptor needs to be lowered inside the column tube 9. The design of the locking means 16 can of course vary. Furthermore a lid 27 and a lid support 29 are provided above the column tube 9 and upper flange 14 and connected to the stand 3 in order to support the chromatography system structure and aid maintenance This is according to conventional models of chromatography systems.

Figure 1B:
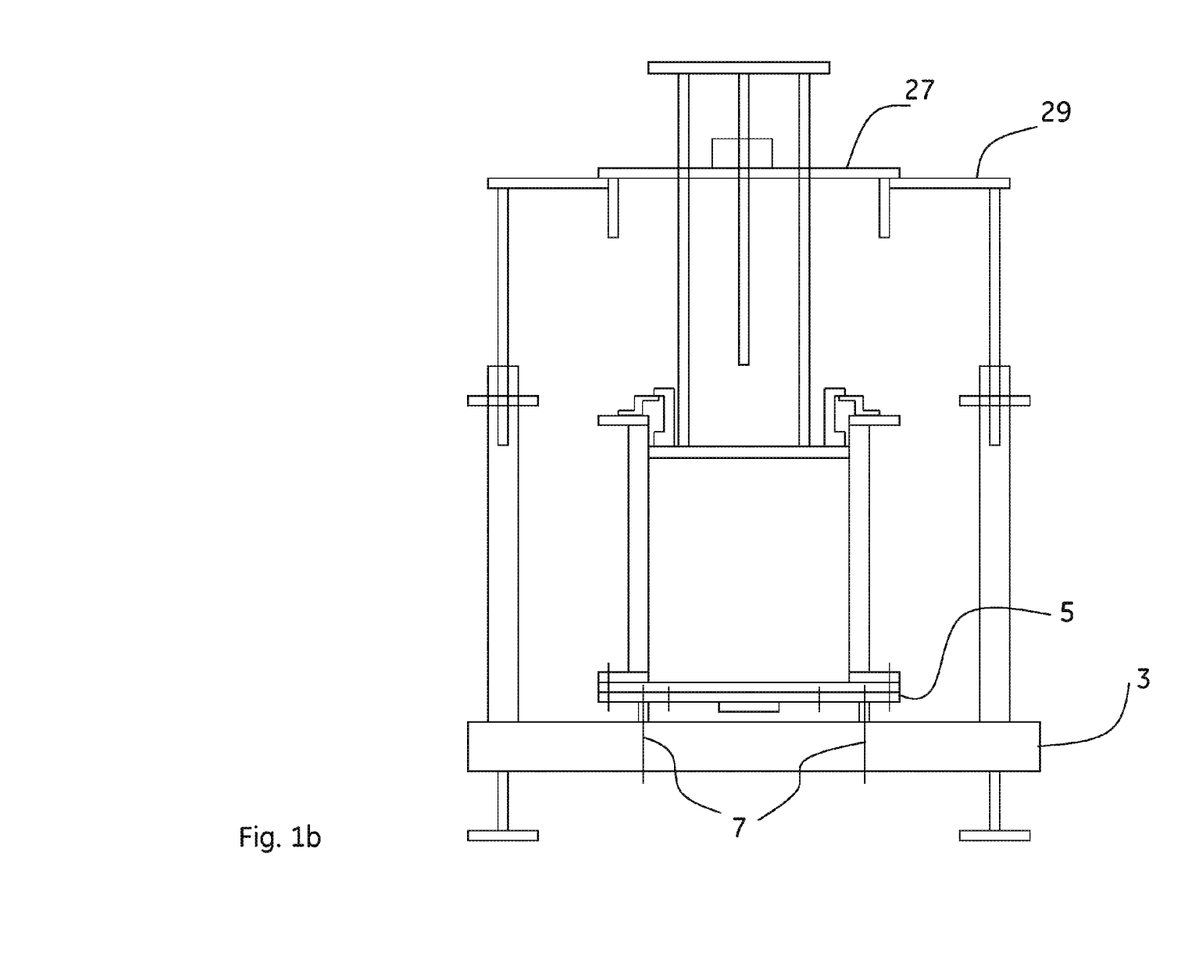

In FIG. 1b the chromatography system of FIG. 1a is shown schematically in a second position where the lid 27 and lid support 29 have been lifted up to a second position. The bolt 7 (detachable joint) securing the bottom plate 5 to the stand 3 is also released now.

Figure 1C:
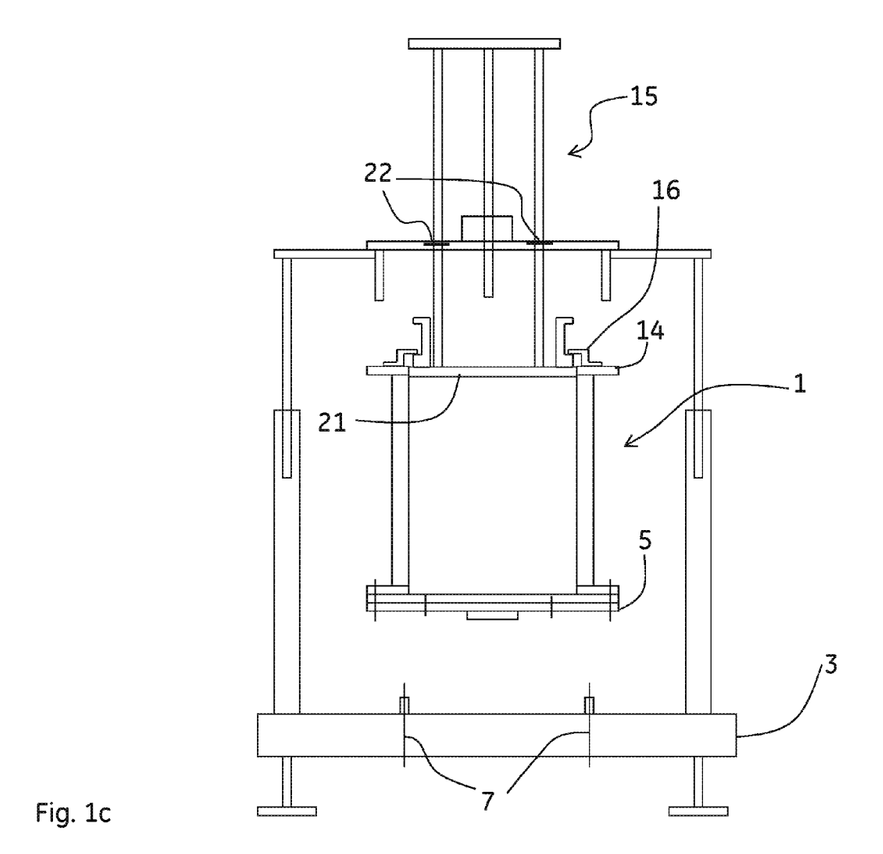

In FIG. 1c the chromatography system of FIG. 1a is shown schematically in a third position where the adaptor 15 is raised. Because of the locking means 16 securing the adaptor stop 23 and thus the adaptor backing plate 21 to the upper flange 14 of the chromatography column 1 and because the detachable joint 7 between the bottom plate 5 and the stand 3 has been released the chromatography column 1 will be raised above the stand 3 together with the adaptor 15. Hereby there will be a space below the bottom plate which can be used when access is needed to the underside of the chromatography column 1 for performing maintenance of the system.

Furthermore a lock sprint 22 is possibly provided in order to secure the adaptor and the chromatography column in the raised position.

Figure 2:
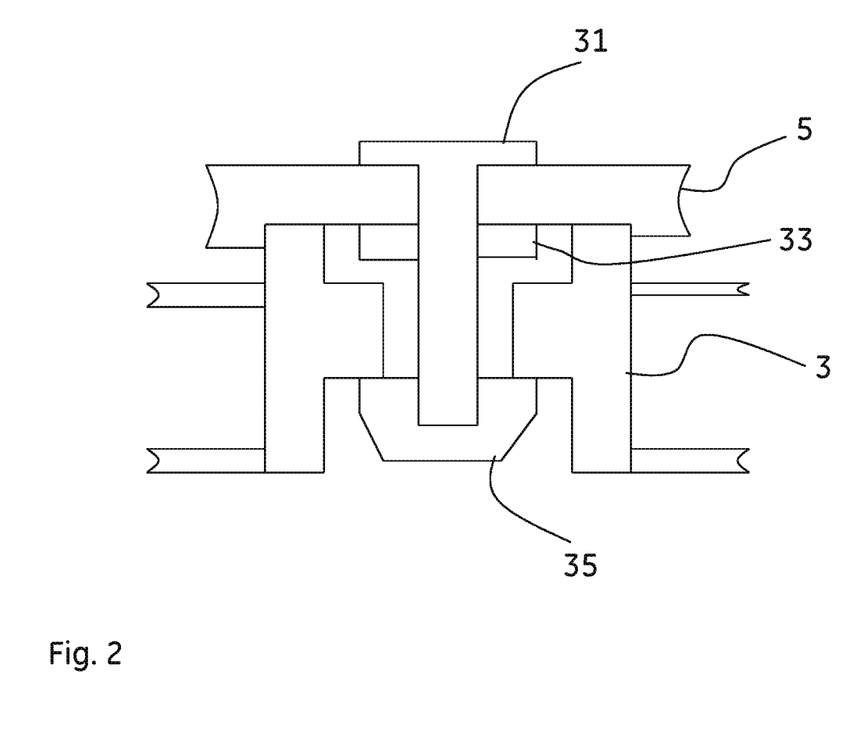
FIG. 2 shows schematically one example of a nut securing the bottom plate to the stand.

FIG. 2 shows schematically in more detail the detachable joint 7 according to one embodiment of the invention. The bottom plate 5 and the stand 3 are shown partly in this view. The detachable joint 7 comprises a bolt 31, a lock nut 33 and a nut 35. The detachable joint 7 can of course be deigned differently.

Figure 3:
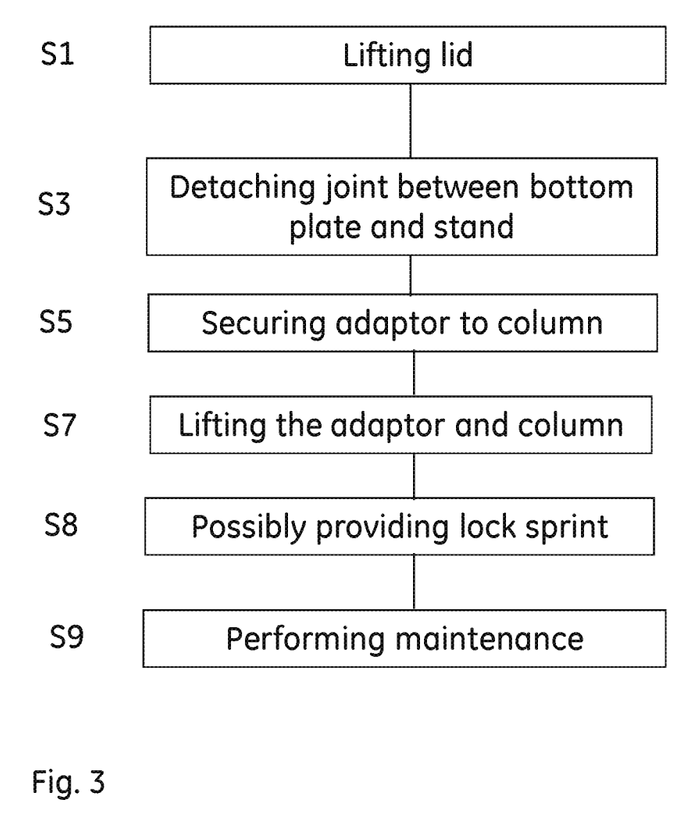
FIG. 3 is a flow chart of a method according to one embodiment of the invention that can be performed on the chromatography system of FIGS. 1a-1c.

FIG. 3 is a flow chart of a method according to one embodiment of the invention that can be performed on the system shown in FIGS. 1a-1c. The method steps are described in order below:

S1: Lifting the lid 27 and lid support 29 to a first position.

S3: Detaching the detachable joint 7 between the bottom plate 5 and the stand 3.

S5: Securing the adaptor 15 to the chromatography column, here the upper flange 14 of the chromatography column (if not already done).

S7: Lifting the adaptor 15 together with the rest of the chromatography column 1.

S8: Possibly providing a lock sprint for securing the adaptor 15 and the chromatography column 1 in the raised position.

S9: Performing maintenance beneath the bottom plate 5.

FIGS. 4a-4d show schematically a chromatography system according to another embodiment of the invention in different positions of a method according to one embodiment of the invention. In FIGS. 4a-4d the chromatography system comprises a chromatography column 41 on a stand 43 with a swing out feature, i.e. a column tube 45 together with an upper flange 47 and a bottom flange 49 can be separated from an upper lid 51 and a bottom plate 53 and then rotated out from these parts. The bottom plate 53 comprises here also a distributor 54. The column tube 45 is all time supported by the stand 43.

Figure 4A:
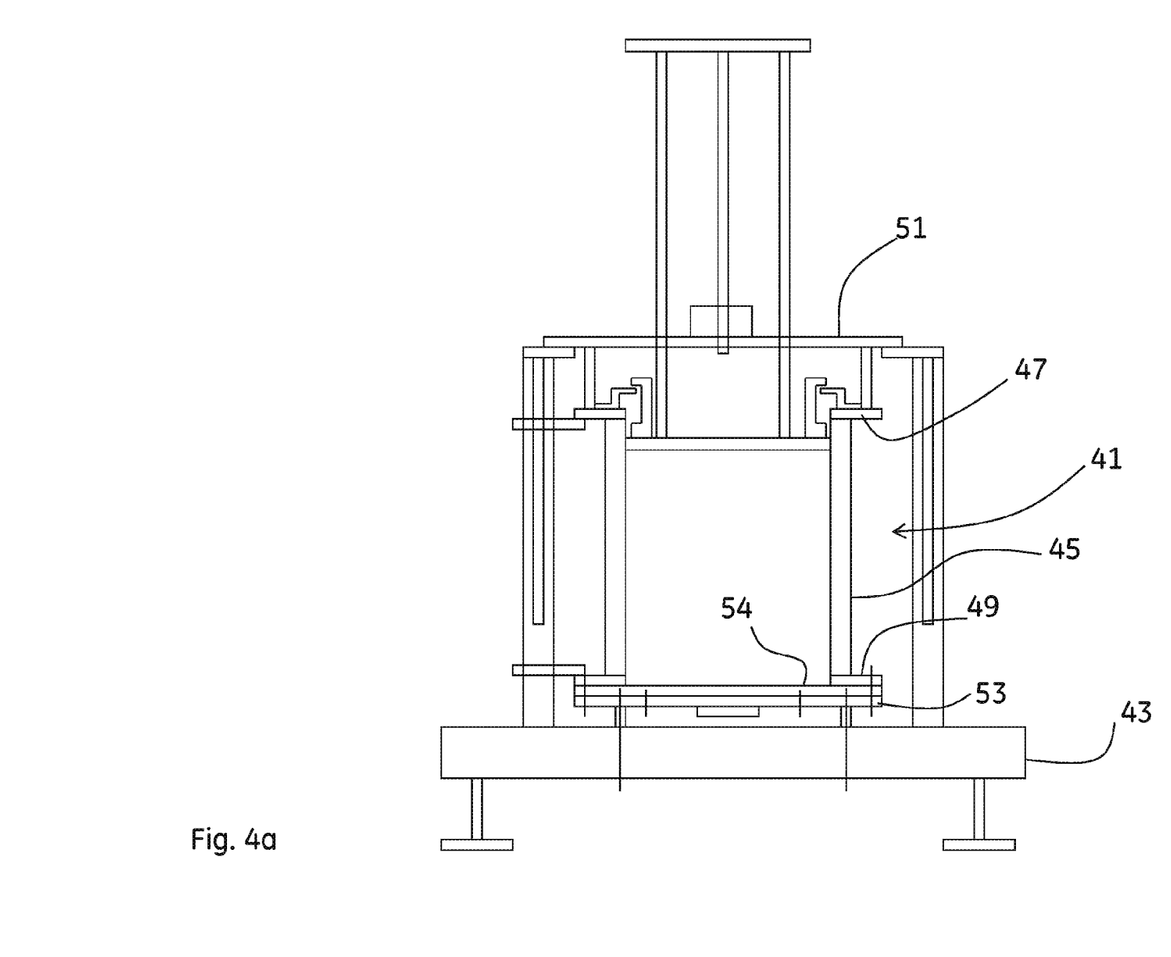
FIGS. 4a-4d show schematically a chromatography system according to another embodiment of the invention in different positions of a method according to one embodiment of the invention.
Figure 4B:
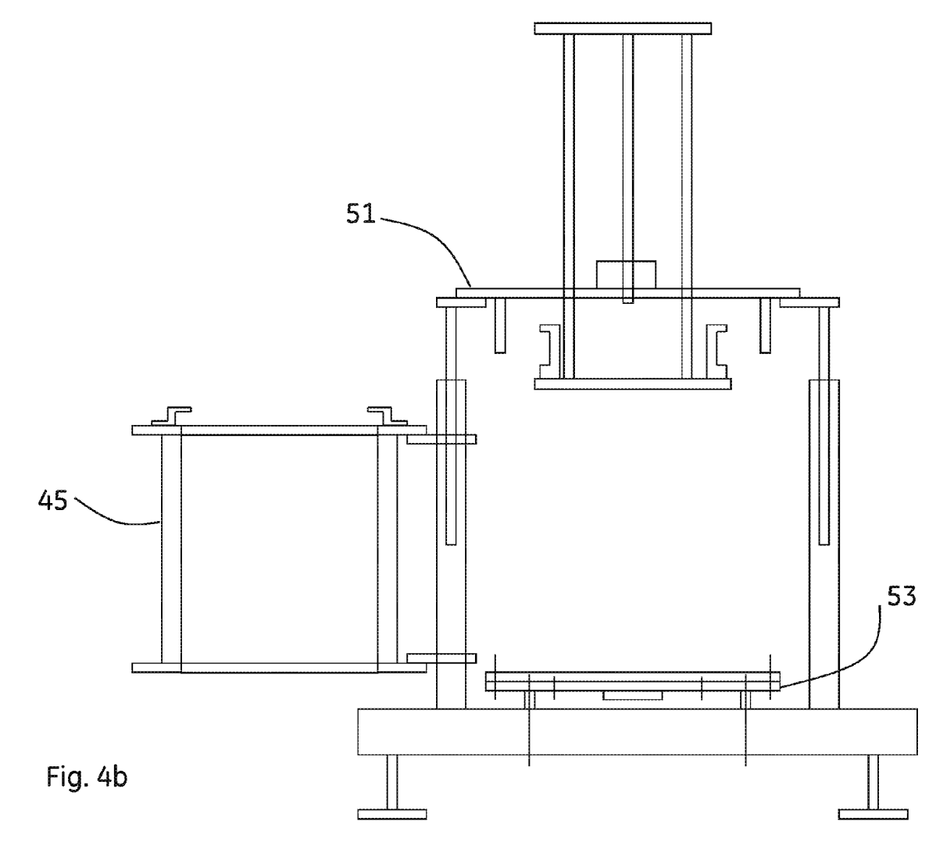
Figure 4C:
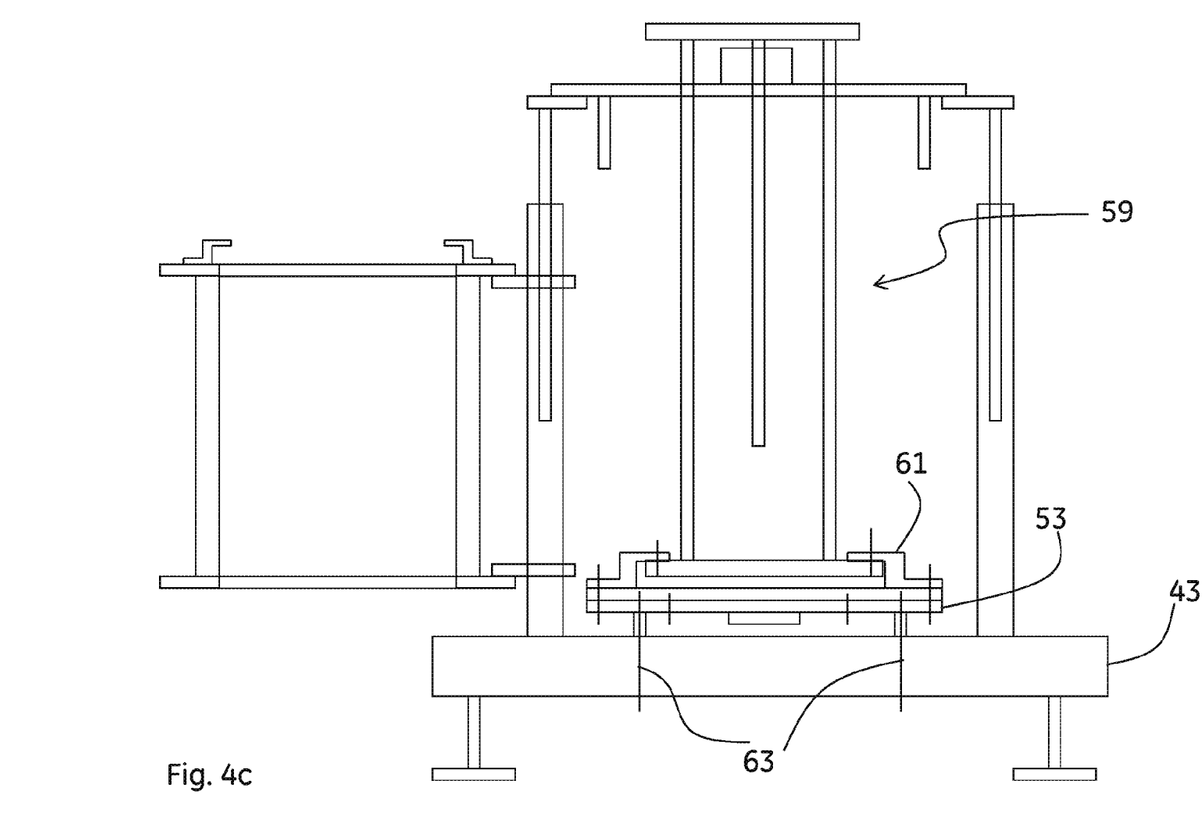
Figure 4D:
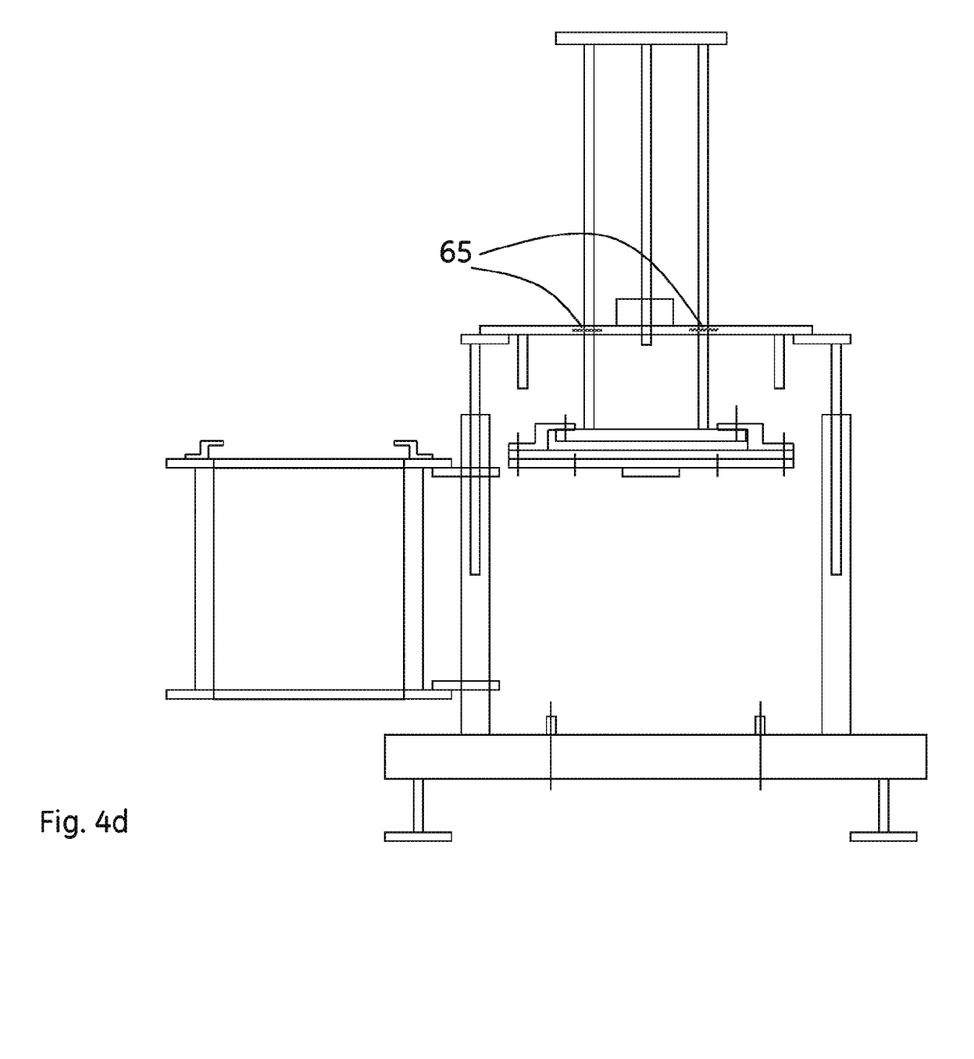
Figure 5:
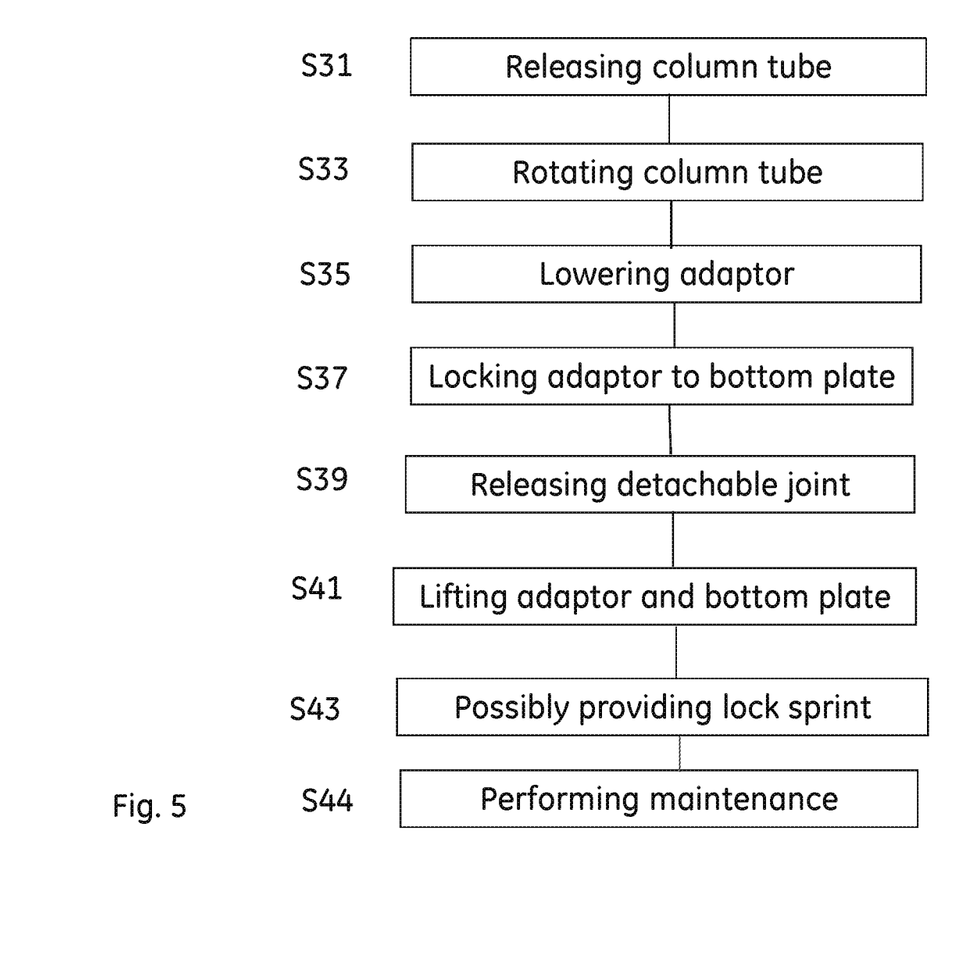
FIG. 5 is a flow chart of a method according to one embodiment of the invention that can be performed on the chromatography system shown in the FIGS. 3a-3d.

FIG. 5 is a flow chart of a method according to one embodiment of the invention that can be performed on the chromatography system shown in the FIGS. 4a-4d. The method steps are described in order below and with reference to the corresponding FIGS. 4a-4d.

S31: The column tube 45 is released from the upper lid 51 and the bottom plate 53.

S33: The column tube 45 is rotated out from the upper lid 51 and the bottom plate 53. This is shown in FIG. 4b.

S35: An adaptor 59 of the chromatography column 41 is lowered almost all the way down to the distributor 54 and the bottom plate 53. This is shown in FIG. 4c.

S37: The adaptor 59 is locked to the bottom plate 53 by a locking means 61. This is shown in FIG. 4c. The locking means 61 can be designed in different ways. In this shown embodiment one part of the locking means is attached to the adaptor by a bolt and another part of the locking means is attached to the bottom plate by another bolt.

S39: A detachable joint 63 between the bottom plate 53 and the stand 43 is released.

S41: The adaptor 59 is lifted together with the bottom plate 53, suitably to a height that is sufficient for a person to sit beside it and conveniently perform the maintenance required, such as unbolting and changing valves on the underside of the chromatography column 41. This is shown in FIG. 4d.

S43: Possibly a lock sprint 65 (shown in FIG. 4d) is provided to lock the adaptor 59 and the bottom plate 53 in the raised position.

S44: Performing maintenance beneath the bottom plate of the column.

One advantage with the invention is that access to the bottom side of the bottom plate is provided without increasing the total height of the chromatography system.

Figure 6:
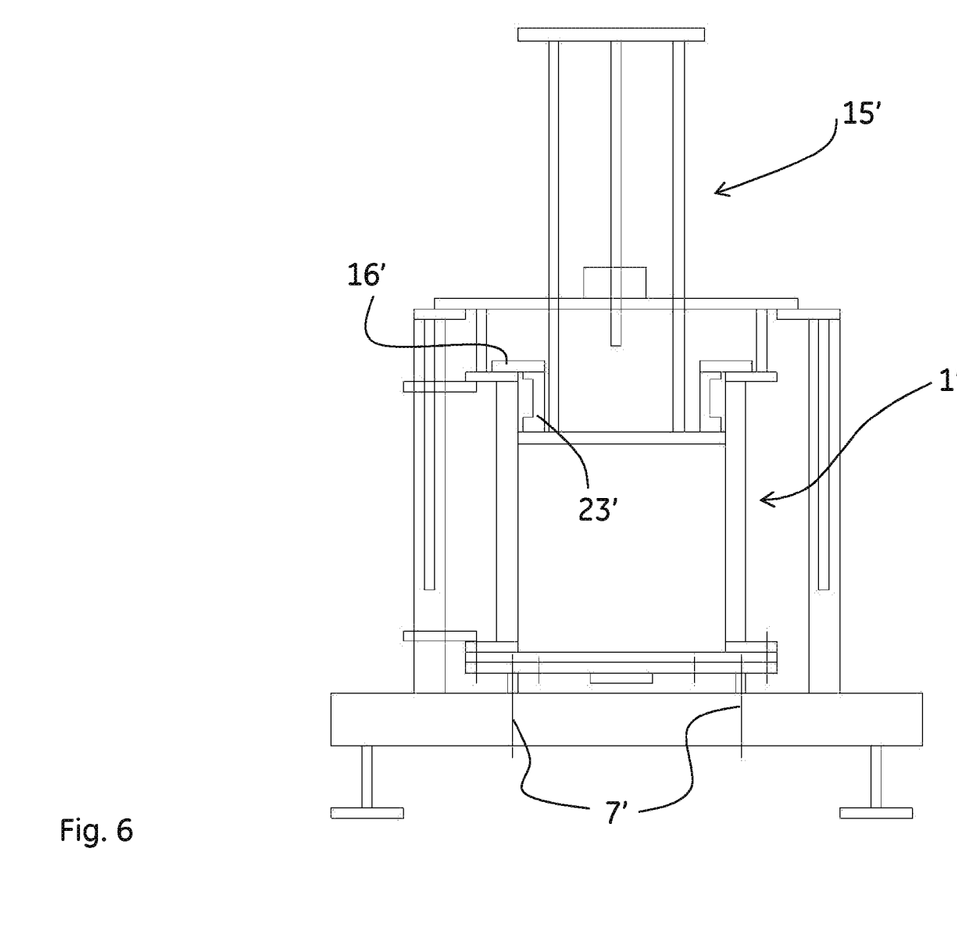
FIG. 6 shows schematically a chromatography system according to another embodiment of the invention.

FIG. 6 shows schematically a chromatography system according to another embodiment of the invention. Most of the parts here are the same as the parts described in FIGS. 1a-1c and these parts will not be mentioned here. The difference in this embodiment is the design of the locking means 16'. In this embodiment an adaptor stop 23' is designed similar to the design of the adaptor stop 23 in FIGS. 1a-1c. The adaptor stop 23' is arranged to engage with a locking means 16' that is secured to the chromatography column 1' when the adaptor 15' is moving upwards when maintenance below the chromatography column is needed. Alternately the locking means 16' could be arranged to engage directly with the adapter in a construction without adapter stop. For lifting the column with the adapter during maintenance a detachable joint 7' needs also to be detached as described in relation to FIGS. 1a-1c. The locking means 16'is a detachable part.

The invention claimed is:

1. A chromatography system comprising a chromatography column (1; 1'; 41) and a stand (3; 43) onto which the chromatography column is provided, characterised in that a bottom plate (5; 53) of the chromatography column is detachably attached to the stand (3; 43) by a detachable joint (7; 7'; 63) and in that a locking means (16; 16'; 61) is provided which during maintenance of the chromatography column can lock an adaptor (15; 15'; 59) of the chromatography system to any part of the chromatography column (1; 1'; 41) making it possible to by lifting the adaptor (15; 15'; 59) also lift the bottom plate (5; 53) from the stand (3; 43) when the bottom plate is released from the stand, wherein a column tube (45) of the chromatography column (41) is adapted to be rotated out from a lid (51) and the bottom plate (53) of the chromatography column (41) during maintenance and wherein the locking means (61) is adapted to lock the adaptor (59) to the bottom plate (53).

2. The chromatography system of claim 1, further comprising a lock sprint (22; 65) adapted to lock the adaptor (15; 59) and the bottom plate (5; 53) in the raised position.

\* \* \* \* \*